United States Patent
Blew et al.

(10) Patent No.: US 8,996,103 B2
(45) Date of Patent: Mar. 31, 2015

(54) SHEET CONDUCTANCE/RESISTANCE MEASUREMENT SYSTEM

(71) Applicant: Lehighton Electronics, Inc., Lehighton, PA (US)

(72) Inventors: Austin Blew, Lehighton, PA (US); Michael Bronko, Lehighton, PA (US); Steven C. Murphy, Pottsville, PA (US); Steve Bell, Ashland, PA (US)

( * ) Notice: Subject to any disclaimer, the term of this patent is extended or adjusted under 35 U.S.C. 154(b) by 0 days.

(21) Appl. No.: 13/868,482

(22) Filed: Apr. 23, 2013

(65) Prior Publication Data

US 2014/0103917 A1 Apr. 17, 2014

Related U.S. Application Data

(63) Continuation of application No. 11/595,306, filed on Nov. 10, 2006, now Pat. No. 8,428,706.

(60) Provisional application No. 60/736,416, filed on Nov. 14, 2005.

(51) Int. Cl.
*A61B 5/00* (2006.01)
*A61B 5/02* (2006.01)
*A61B 5/053* (2006.01)
(Continued)

(52) U.S. Cl.
CPC ............ *G01N 27/04* (2013.01); *A61B 5/02028* (2013.01); *A61B 5/053* (2013.01); *G01N 27/023* (2013.01); *G01N 27/028* (2013.01)
USPC ......................................................... 600/547

(58) Field of Classification Search
USPC ......................................................... 600/547
See application file for complete search history.

(56) References Cited

U.S. PATENT DOCUMENTS

| 4,029,957 A | 6/1977 | Betz et al. |
| 4,087,745 A | 5/1978 | Kennedy et al. |
| 4,605,893 A | 8/1986 | Braslau |

(Continued)

FOREIGN PATENT DOCUMENTS

| CH | 419670 | 1/1965 |
| DE | 2309889 | 8/1974 |

(Continued)

OTHER PUBLICATIONS

PCT/ISA/237 Written Opinion of the International Searching Authority for PCT/US05/28254.

(Continued)

*Primary Examiner* — Max Hindenburg
(74) *Attorney, Agent, or Firm* — Duane Morris LLP

(57) ABSTRACT

An apparatus for testing of electrical or physical properties of a material include a single coil sensor mounted adjacent to a sample of the material. Sheet conductance of a wide variety of materials may be measured using the single coil to determine if the material conforms to generally accepted standards for the use to which the material will be put. In some examples, the material is a semiconductor wafer or flat panel. In other examples, the material is the body tissue of a patient. A non-invasive technique using the apparatus is also disclosed for monitoring the health of patient tissue such as musculature, and/or to determine whether healthy circulation is present, by measuring the conductance of the patient tissue in response to a magnetic field applied by the single coil. The single coil may be hand held, or it may be movable using an automated positioning system under computer control.

12 Claims, 10 Drawing Sheets

(51) Int. Cl.
*G01N 27/02* (2006.01)
*G01N 27/04* (2006.01)

(56) References Cited

U.S. PATENT DOCUMENTS

| | | | |
|---|---|---|---|
| 4,618,938 | A | 10/1986 | Sandland et al. |
| 4,636,634 | A | 1/1987 | Harper et al. |
| 4,727,330 | A | 2/1988 | Funk |
| 4,786,042 | A | 11/1988 | Stemmle |
| 4,818,169 | A | 4/1989 | Schram et al. |
| 4,856,904 | A | 8/1989 | Akagawa |
| 4,865,677 | A | 9/1989 | Matsushita et al. |
| 4,875,092 | A | 10/1989 | Yamanishi et al. |
| 4,893,322 | A | 1/1990 | Hellmick et al. |
| 4,914,452 | A | 4/1990 | Fukawa |
| 5,044,752 | A | 9/1991 | Thurfjell et al. |
| 5,103,182 | A | 4/1992 | Moslehi |
| 5,111,963 | A | 5/1992 | Grace, Sr. |
| 5,154,082 | A | 10/1992 | Mintz |
| 5,179,333 | A | 1/1993 | Washizuka et al. |
| 5,196,786 | A | 3/1993 | Usami et al. |
| 5,233,195 | A | 8/1993 | Hellstrom et al. |
| 5,406,092 | A | 4/1995 | Mokuo |
| 5,488,292 | A | 1/1996 | Tsuta |
| 5,609,333 | A | 3/1997 | Mandel et al. |
| 5,619,145 | A | 4/1997 | Matsuda et al. |
| 5,645,391 | A | 7/1997 | Ohsawa et al. |
| 5,670,888 | A | 9/1997 | Cheng |
| 5,781,018 | A | 7/1998 | Davidov et al. |
| 6,100,703 | A | 8/2000 | Davidov et al. |
| 6,147,356 | A | 11/2000 | Hahn et al. |
| 6,202,482 | B1 | 3/2001 | Blew et al. |
| 6,205,852 | B1 | 3/2001 | Blew |
| 6,211,514 | B1 | 4/2001 | Schultz et al. |
| 6,280,103 | B1 | 8/2001 | Zawodny et al. |
| 6,443,002 | B2 | 9/2002 | Blew et al. |
| 6,452,660 | B1 | 9/2002 | Nguyen-Nhu |
| 6,462,538 | B2 * | 10/2002 | Harada ............... 324/224 |
| 6,549,006 | B2 | 4/2003 | Le |
| 6,657,439 | B1 | 12/2003 | Harada |
| 6,711,948 | B2 | 3/2004 | Blew et al. |
| 6,771,372 | B1 | 8/2004 | Traber |
| 6,791,339 | B2 | 9/2004 | Licini et al. |
| 6,794,886 | B1 | 9/2004 | Chen et al. |
| 7,109,724 | B2 | 9/2006 | Eberhardt et al. |
| 2001/0004210 | A1 | 6/2001 | Harada |
| 2004/0100277 | A1 | 5/2004 | Tam |
| 2004/0015326 | A1 | 8/2004 | Suh |

FOREIGN PATENT DOCUMENTS

| | | |
|---|---|---|
| EP | 0674340 A1 | 9/1995 |
| EP | 1957965 | 8/2008 |
| EP | 2439521 | 4/2012 |
| GB | 2335971 | 10/1999 |
| JP | 61-173144 | 8/1986 |
| JP | 2001-165970 | 6/2001 |
| JP | 2005-140564 | 6/2005 |
| KR | 10-0381062 | 4/2003 |
| TW | 424134 B | 3/2001 |

OTHER PUBLICATIONS

PCT/ISA/220 Written Opinion of the International Searching Authority for PCT/US2006/060780.
PCT/ISA/220 International Search Report for PCT/US2006/060780.
PCT/ISA/210 International Search Report for PCT/US2005/28254.
Office Action dated Oct. 29, 2012 issued in corresponding Korean Patent Application No. 10-2008-7014074.
Extended European Search Report dated Jan. 31, 2012 in corresponding European Patent Application No. 12150138.1-1240, 4 pages.
Office Action dated Aug. 28, 2012 issued in corresponding Japanese Patent Application No. 2008-540358.

* cited by examiner

SHEET CONDUCTANCE/RESISTANCE MEASUREMENT SYSTEM

CROSS-REFERENCE TO RELATED APPLICATIONS

This is a non-provisional of U.S. Provisional Patent Application Ser. No. 60/736,416, filed Nov. 14, 2005, titled "Single Coil Sheet Conductance/Resistance Measurement System," the entirety of which application is incorporated herein by reference.

FIELD OF THE INVENTION

The invention generally relates to an improved system for measuring the sheet conductivity of a material sample, and more particularly to a design for a single coil measurement system for determining the sheet conductivity of a wise variety of types of material samples, including human body tissue.

BACKGROUND

After fabrication, and after various steps during processing, samples such as glass panels, semiconductor wafers, and other materials are often tested for a variety of physical, electrical, mechanical and chemical properties. One such test that is often performed on sheet samples is to measure the sample's sheet conductance. In one example, the sheet conductance (and/or resistance) of a semiconductor wafer is measured to ensure the absence of undesirable sheet resistance variations in epitaxial or ion implanted and annealed wafers, prior to adding expensive subsequent processing steps required to produce integrated circuits.

It is known that sheet conductance may be measured as a proportional DC voltage. Knowledge of the sheet conductance of a material sample is important, because it allows for the early identification of defects in the material prior to undertaking subsequent expensive process steps that are required to produce modern integrated circuit devices. If the sample does not conform to a known sheet conductance profile, then it may be presumed that a defect is present in the wafer or in a portion of the wafer, and the wafer may be scrapped, or further processing steps may be performed taking into account the defect(s).

Current methods and systems for measuring sheet resistance of a sample typically use a two coil configuration, with one coil positioned on opposite sides of the sample under test. The benefit of such two-coil configurations is that they provide two magnetic fields that penetrate the sample or samples, and thus the sample is subjected to a relatively evenly distributed field, which is important for purposes of obtaining an accurate sheet resistance measurement. The disadvantages of such two-coil systems are that the two coils must be placed close enough to each other in order for the eddy current process to be effective, which thus limits the overall thickness of the sample being measured. Additionally, for so-called "series aiding" two-coil systems, measurement of large-diameter samples requires longer lead lengths between the coils, which can result in problems with frequency and loss, thus reducing the stability of the circuit that generates the magnetic field. As a result, the measurements obtained may have a less than desired accuracy.

Furthermore, it may be difficult and time consuming to move large samples in and out of the opposing coils, and to position them appropriately when a plurality of measurement locations are involved.

Thus, there is a need for an improved system for measuring sheet conductance of material samples. Specifically, there is a need for a sheet conductance testing device that is easily movable and positionable with respect to the sample to enable testing without extensive handling and positioning of the sample, thus eliminating the need for a sample to be moved between a pair of coils, and thereby enabling practical testing of larger and thicker samples.

There is also a need for a device that can be used to test materials other than traditional semiconductor and/or flat panel materials. For example, it would be desirable to provide a non-invasive system and technique for performing conductance measurements in aid of a variety of diagnostic medical analyses, such as the monitoring of blood circulation and oxygenation of human tissue. Prior art techniques using ultrasound are capable only of showing, for example, whether a blood vessel is allowing satisfactory circulation, but still may not show whether oxygen from the circulated blood is being adequately moved to the surrounding tissue, to thereby provide a gauge of the general health of the tissue. Thus it would be advantageous to provide a system that can identify situations in which blood circulation is satisfactory, but nonetheless where tissue may still be dying. Such systems would advantageously provide information to medical personnel that is not currently available through non-invasive techniques.

SUMMARY OF THE INVENTION

The disadvantages heretofore associated with the prior art are overcome by the inventive design for a single coil sheet conductance/resistance measurement system.

A system is disclosed for measuring conductance of a material sample, comprising a coil for creating a magnetic field adjacent to a sample to be tested, an oscillator connected to the coil for applying a voltage to the coil, and an automatic gain control circuit connected to the oscillator for sensing a voltage change caused by the sample when the sample is positioned adjacent to the coil and exposed to the magnetic field, wherein the voltage change is proportional to a conductance of the sample.

The system may further comprise a movable housing, wherein the coil, oscillator and automatic gain control circuit are contained within the housing such that a portion of the coil is positionable adjacent the sample to expose the sample to the magnetic field. The system may further comprise an automatic adjustment assembly and a computer controller, the automatic adjustment assembly being connected to the movable housing to automatically position the coil at a desired location with respect to the sample. The automatic adjustment assembly may be adjustable along three mutually perpendicular axes, wherein the computer controller is programmed to move the automatic adjustment assembly to a desired position in response to a user command or a pre-programmed routine.

The system may further comprise an offset sensor and a feedback control loop. The offset sensor may be configured for measuring a distance between the coil and the sample and communicating information relating to said distance to said computer controller via said feedback loop. The computer controller may be operable to automatically adjust the position of the coil with respect to the sample to maintain a predetermined distance between the coil and the sample. The system may further comprise a memory associated with the coil, the memory being capable of storing a plurality of conductance values for said sample. A processor may be associated with the memory, the processor being configured to execute instructions for developing trend information from said plurality of conductance values.

A method for measuring conductance of a sample is also disclosed, comprising: providing a coil, an oscillator connected to the coil for applying a voltage to the coil do induce said magnetic field, and an automatic gain control circuit connected to the oscillator; positioning said coil adjacent a sample to be measured; subjecting the sample to a magnetic field produced by said coil; detecting a change in voltage due to the presence of said sample in said magnetic field; converting said voltage change to a conductance value for said sample; and comparing said conductance value to a standard conductance value to determine whether said conductance value is within a predetermined acceptable range.

The step of positioning said coil may comprise moving the coil to a predetermined offset distance from the sample. The step of positioning the coil may comprise adjusting the position of the coil using an automatic positioning system subject to computer control. The sample may be a portion of a human patient, the method further comprising the step of storing said conductance value and said standard conductance value in a memory element associated with said coil. The step of comparing the conductance value to a standard conductance value may further comprise developing trend information regarding conductance values for said sample and using that trend information to make a treatment decision regarding a patient. The step of comparing the conductance value to a standard conductance value may further comprise comparing a plurality of individual conductance values of the sample measured at a plurality of measurement locations, and comparing said individual conductance values to a plurality of respective standard conductance values.

BRIEF DESCRIPTION OF THE DRAWINGS

The details of the invention, both as to its structure and operation, may be obtained by a review of the accompanying drawings, in which like reference numerals refer to like parts, and in which.

DETAILED DESCRIPTION

A method and apparatus for measuring sheet conductance (mhos/square) of a sample (e.g., semiconductor wafer, flat panel, biological tissue, other conductive material, etc.) using a single sample sensing coil is disclosed.

Figure 1:
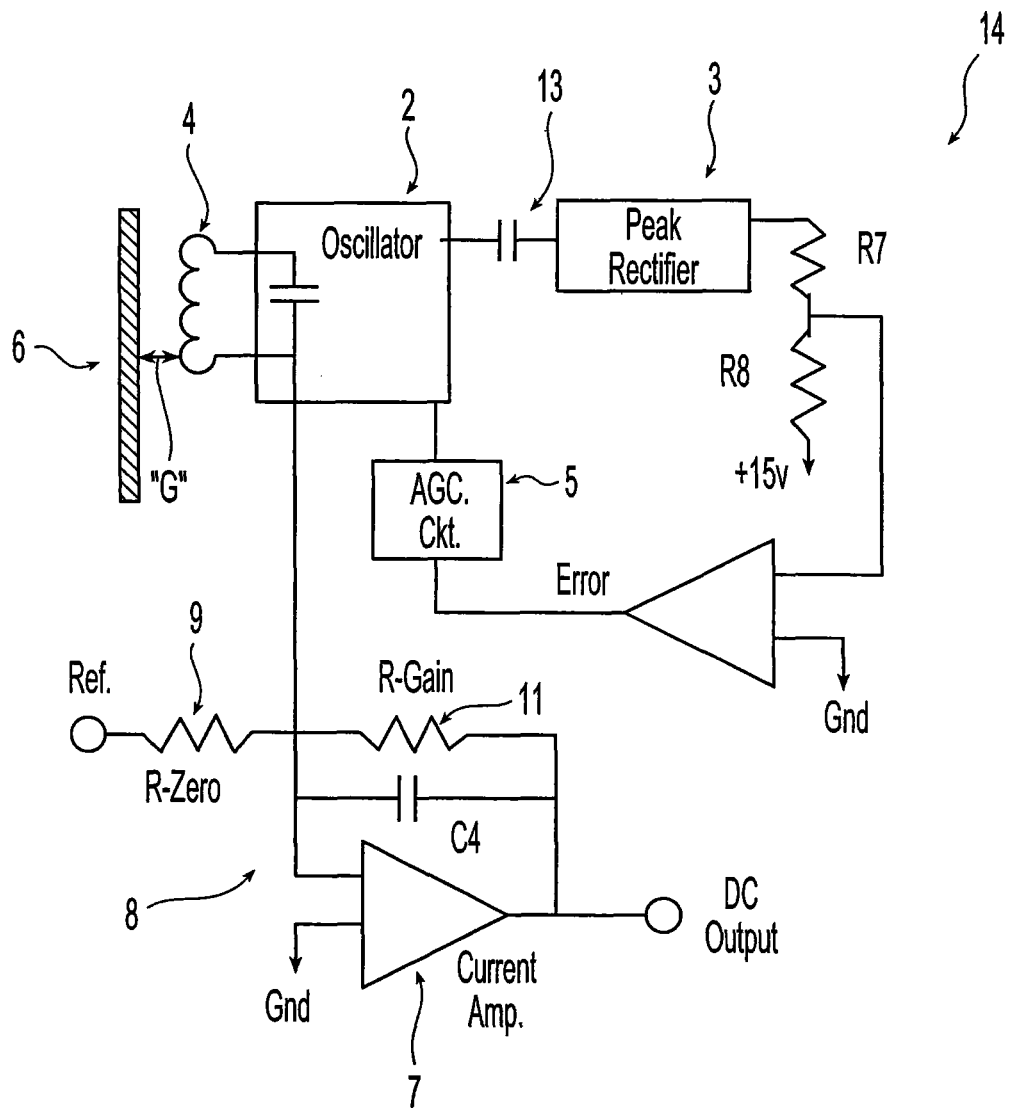
FIG. 1 is a block diagram of a conductance board for use with the inventive single coil test assembly.

Referring to FIG. 1 a circuit diagram of an exemplary, conductance board 14 comprises a single coil 4 and associated circuitry, comprising an oscillator 2, peak rectifier 3, Automatic Gain Control (AGC) circuit 5, current amplifier 7, and zero and gain adjustment potentiometers 9, 11.

In operation, the single coil 4 is positioned adjacent a sample 6 to be tested, and the coil 4—driven by oscillator 2—generates a DC voltage and magnetic field (flux) in proximity to the sample 6. Included with a capacitor 13 in the potted circuit board module 14 is part of the tank circuit of a marginal oscillator 2. An approximately 3V peak-to-peak voltage output is applied to the sample 6, and is controlled by the AGC 5. When the sample 6 is tested, the peak-to-peak amplitude is decreased depending on the conductance of the sample 6, causing Joule heating losses, etc. The AGC 5 senses this decrease and additional current is applied to obtain the original peak-to-peak voltage. The additional current applied is proportional to the sheet conductance of the sample 6 being tested.

Figure 2:
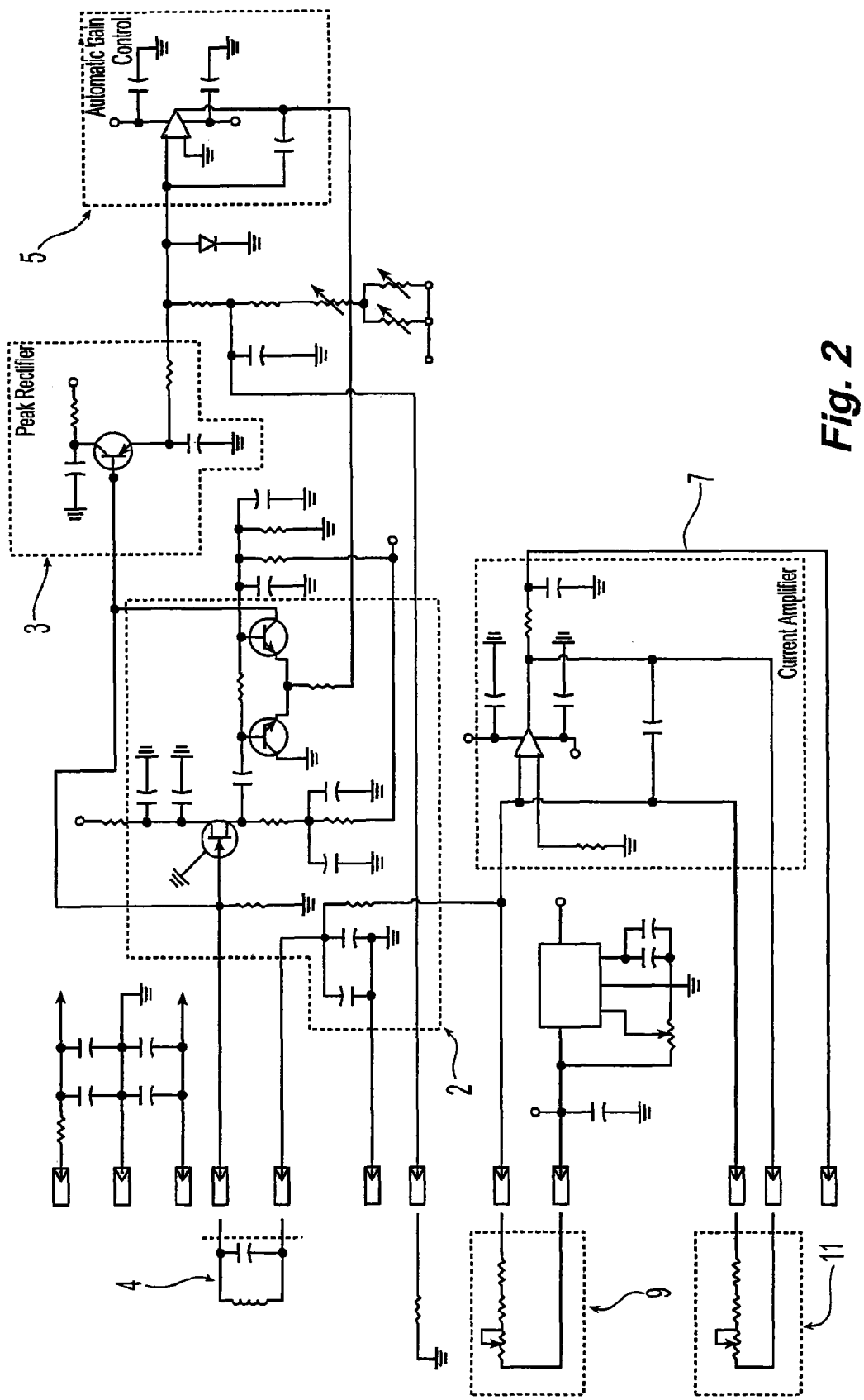
FIG. 2 is a detailed schematic of the conductance board of FIG. 1.

In order to correlate the voltage change to a conductance value of the sample 6, the system may first be calibrated using a standard wafer, tissue phantom or similar calibration sample having known properties. To do this, the circuitry—which may be composed of integrated circuit op amps (see FIG. 2)—may be zeroed without a sample. The standard may then be placed adjacent to the coil 4 and the circuit gain adjusted by means of a feedback resistor in an op amp, or other appropriate method, to obtain the proper temperature-corrected output according to the standard value. When the test sample 6 is then placed adjacent to the coil 4, the voltage signal will vary as it relates to the sheet conductance of the sample 6.

Again referring to FIG. 1, monitoring the AGC 5 of oscillator 2 that drives coil 4 generates a DC voltage, the sample-sensing coil 4 provides a magnetic field adjacent to the sample 6. The amount of energy the sample absorbs by creating Eddy currents causes the oscillator power to change. The AGC compensates for this change in energy, thus producing a DC voltage change. The system measures the DC voltage prior to moving the sample 6 adjacent to the coil 4 and after the sample is moved adjacent to the coil 4. The difference in the proportional DC voltage (i.e. the difference between the measurements with and without a sample adjacent the coil 4) may be captured by a computer or voltmeter to calculate or otherwise determine the sheet conductance of the sample 6. This determination may include the incorporation of an inverter circuit to obtain sheet resistance or bulk resistivity, wherein sheet resistance is the inversion of the sheet conductance. Bulk resistivity can also be calculated from the sheet resistance value with a known (entered or measured) thickness. In the case of samples with high resistance, the test method may further include a "rail calibration" step, which compensates for the magnetic signature of handler rails, if used to support or move the sample 6.

Figure 3:
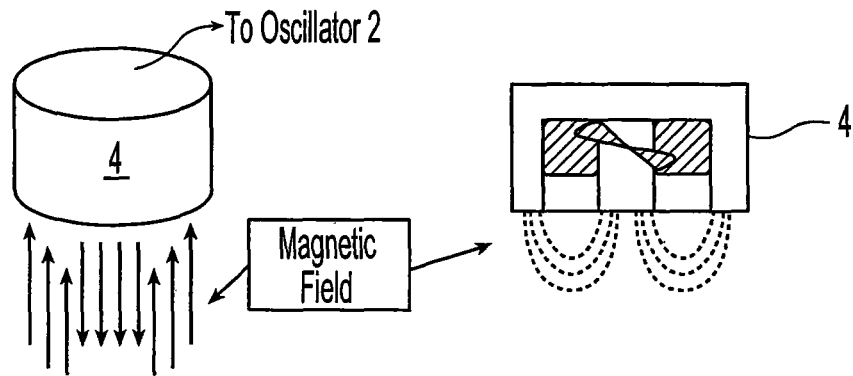
FIG. 3 shows the magnetic fields associated with a single coil test assembly.
Figure 4:
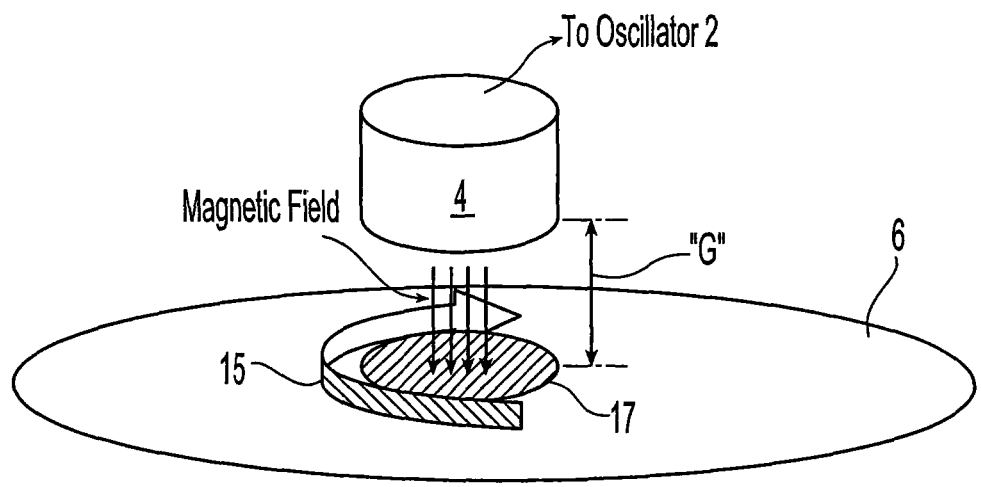
FIG. 4 shows the eddy current effect on a sample exposed to the magnetic fields shown in FIG. 3.

FIG. 3 shows a "single" coil 4 arrangement with an instantaneous magnetic RF field. A cross-section of a cup core coil 4 is shown with associated magnetic field to which the sample 6 will be subjected. FIG. 4 shows the eddy current effect on a sample 6 exposed to the magnetic fields of the "single" coil 4 of FIG. 3. The sample 6 is positioned a known gap "G" from the coil 4, and the magnetic field applied, causing eddy currents 15 within a region 17 of the sample subject to the field. It will be appreciated that the area of the magnetic field (and thus the test region 17) will be equal to the area of the ferrite of the "single" coil 4. Note, the gap "G" will be the same distance at which the calibration sample is placed during the calibration step, as previously described.

The benefit of using a single-coil 4 arrangement, as compared to prior dual coil arrangements, is that it may enable versatile measurement of samples 6 having greater or variable thicknesses. It may also reduce the total number of electrical and mechanical components of the system, which may reduce manufacture, repair and material costs. Challenges in designing a single-coil system include the need to maintain the gap "G" (z-axis distance (see FIG. 4)) between the coil 4 and the sample 6 at a constant value within a high tolerance in order to produce measurements having a desired accuracy. Additionally, where the sample under test has an uneven thickness, either due to manufacturing processing or the natural topography of the sample (e.g., the surface of human arms, legs, etc.), constant adjustments may be required in order to ensure that the single coil is appropriately positioned with respect to the sample to ensure the desired gap is maintained. Thus, feedback control systems may be used in combination with the single coil 4 to ensure the desired gap is maintained, as will be described in greater detail later.

The size of the coil may determine the range of the measurement gap "G" between the coil 6 and the sample 4. This "range" represents the measurement detection range from which a standard calibration value can be obtained. The smaller the coil 4, the smaller the overall permissible range of the gap. Thus, for a 2.5" coil, the optimal range of the gap "G" between the coil 4 and sample 6 is from about 5 mils to about 200 mils. For a 1" coil, the optimal range of the "G" between the coil 4 and sample 6 is from about 10 mils to about 80 mils. For a 14 mm coil, this calibration range was found to be about 0 mils to about 10 mils.

Thus, in use, a "standard" material sample (i.e., a sample with a known sheet conductivity) may be placed under the coil 4 and a gap distance "G" may be obtained within one of the aforementioned ranges (depending on the coil size). Again, for a 2.5" coil, this gap distance "G" may be in the range of from about 5 mils to about 200 mils. A "standard" reading or calibration value, at the selected gap value, may then be taken using the coil 4. Once the standard calibration value has been obtained, the standard may be removed and the sample 6 inserted and tested. In order to obtain a desired accuracy of the test readings for the sample, the gap "G" must be maintained as close as possible to the gap value "G" used during the calibration (e.g. if a gap of 100 mils is used in the calibration, then a gap of 100 mils should be maintained when taking the subsequent readings of the sample 6). The inventors have found that in order to obtain an accuracy of the sheet resistance measurement to within +/−3% of expected reading, then the gap should be held to within about +/−0.006" of the gap value used to take the "standard" reading for a 2.5" coil, to within about +/−0.004" of the gap value used to take the "standard" reading for a 1" coil; and to within about +/−0.003" of the gap value used to take the "standard" reading for a 14 mm coil.

As will be appreciated, for small coil sizes (e.g., 14 mm), it may be possible to take sample measurements by simply contacting the coil 4 with the sample 6, or by using a very thin sheet of plastic or other barrier material between the coil and sample. This may eliminate problems associated with maintaining a desired gap "G" between the coil 4 and the sample 6, particularly where an uneven sample topography is encountered. In one example, where the "sample" 6 is a region of a patient's leg, the system may be used to confirm satisfactory permeance of blood through a particular artery. Due to the uneven nature of the leg surface, it may be difficult to ensure a constant gap is maintained between the coil 4 and the skin, and maintenance of a gap may only be possible through the use of an automated positioning system. Thus, it may be easier to simply contact the coil 4 with the skin and measure different areas or segments up or down the leg. It will be appreciated that such a contact method may not be desirable for all cases, such as where the patient being monitored is a burn victim. Additionally, if the sample to be tested is a semiconductor wafer or flat panel, it will typically not be desirable to contact the sample with the coil.

Thus, for cases in which it is desirable to maintain a gap "G" between the coil 4 and sample 6, an automatic positioning device may be integrated into the system to provide constant feedback and positioning/repositioning of the coil 4 with respect to the sample 6. Thus, an automatic positioning device may be used to maintain the desired gap between the coil 4 and the sample 6, as will be described in greater detail later.

Figure 5:
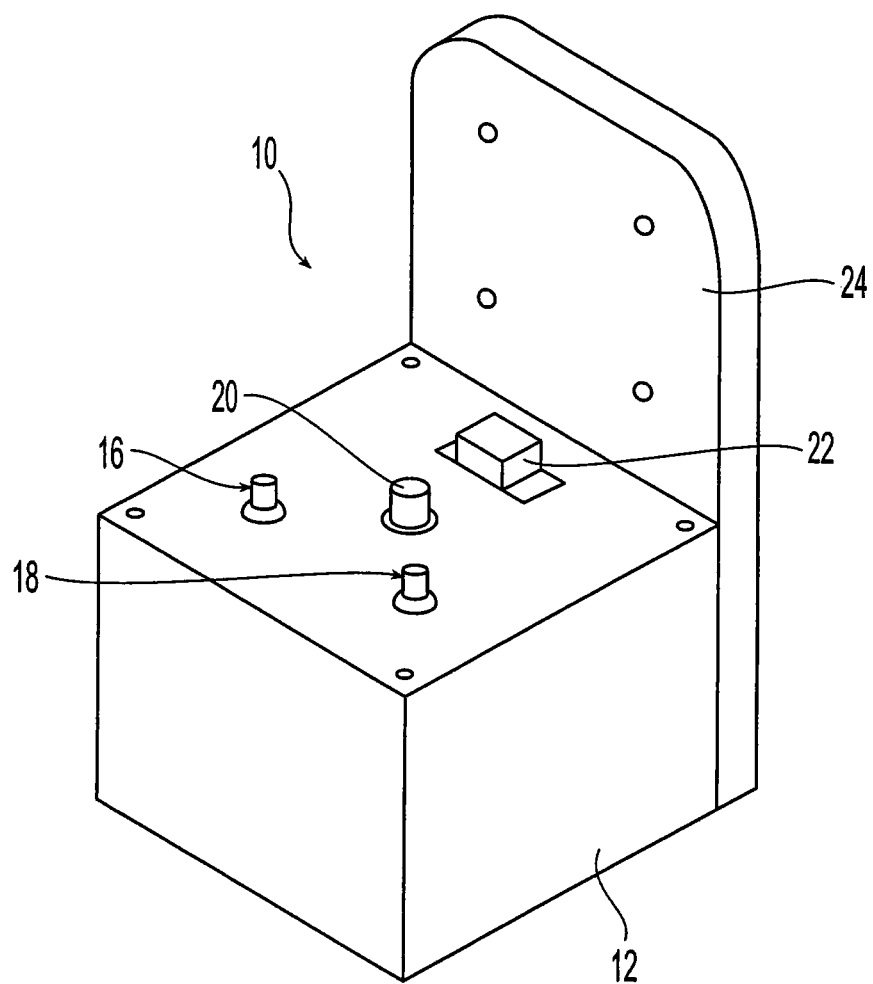
FIG. 5 is an isometric view of a modular housing unit for the single coil test assembly.
Figure 6:
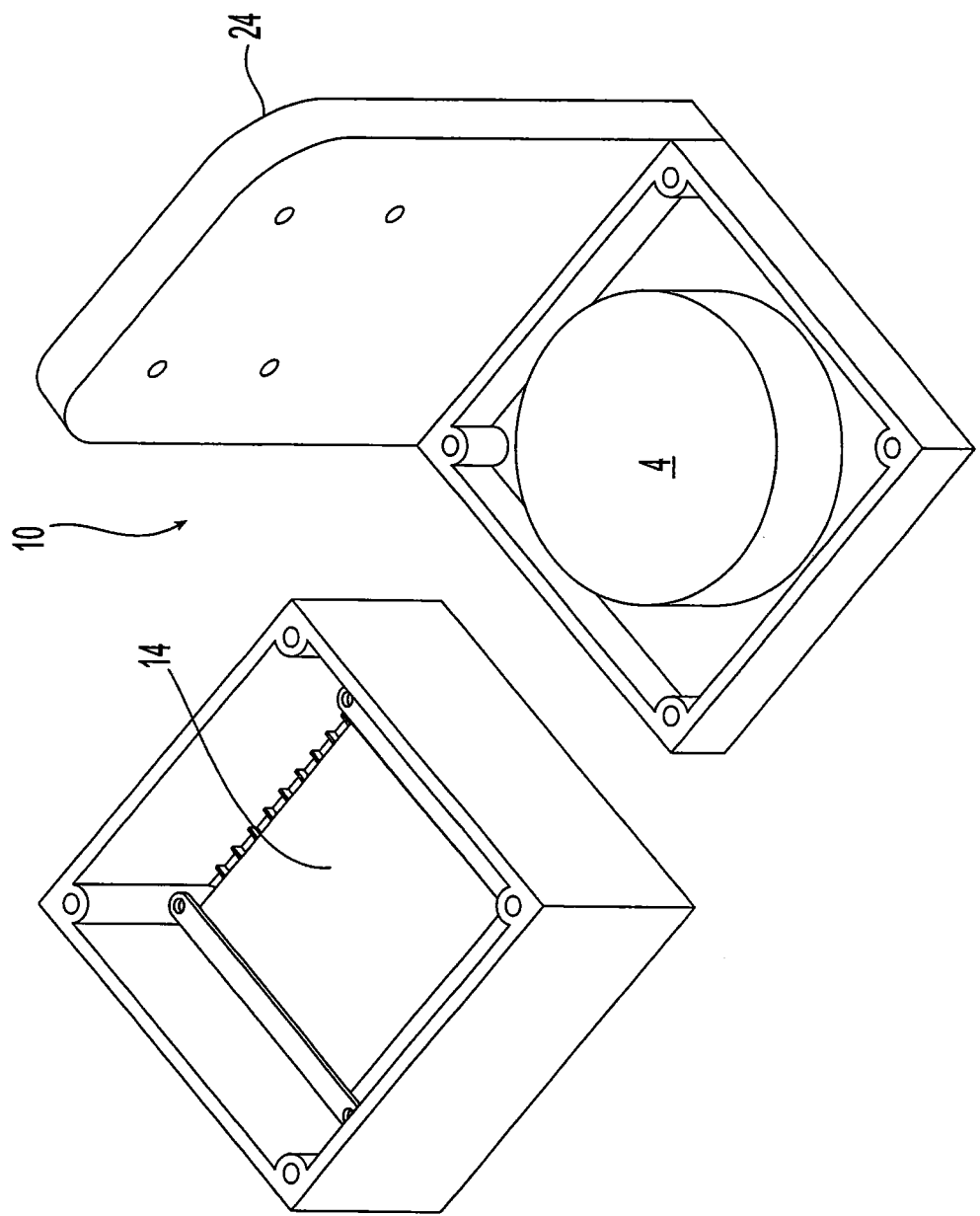
FIG. 6 is an exploded view of the test assembly of FIG. 5, showing placement of the electronics module and single coil within the housing unit.

Referring FIG. 5 a single coil test assembly 10 is shown, including the coil 4 and associated electronics module 14. The assembly 10 allows easy handling, carriage and positioning of the coil and electronics. Thus, the test assembly may comprise a compartment 12 which houses an electronics measurement module 14 and the coil 4. The electronics measurement module 14, as previously described in relation to FIGS. 1 and 2, comprises the circuitry used to drive the coil 4 and to obtain a measurement of a sample 6. FIG. 6 shows the electronics measurement module 14 disconnected from the assembly 10, illustrating the placement of the module within the housing. Provisions are made, as shown on the top, for access to zero and gain adjustment potentiometers 16, 18 (FIG. 5) which are used to calibrate the system. Also shown is a connector 20 for accessing the analog voltage output signal and a pin connector 22 for power input terminations. A bracket 24 is configured for connecting the single coil tester assembly 10 to an automated positioning system, such as that shown in FIG. 7. Not shown are external connections required for delivering power to the unit.

Referring again to FIG. 6, the single coil 4 is mounted directly adjacent to the electronics measurement module 14. This configuration minimizes the distance between the coil 4 and the measurement module 14, which eliminates the need for longer cable length leads, and thus improves the system's signal-to-noise ratio. It will be appreciated that the design of the assembly 10 is not limited to the size of any one particular size coil assembly, and therefore, a variety of different sized coils could easily be used in this configuration.

Figure 7:
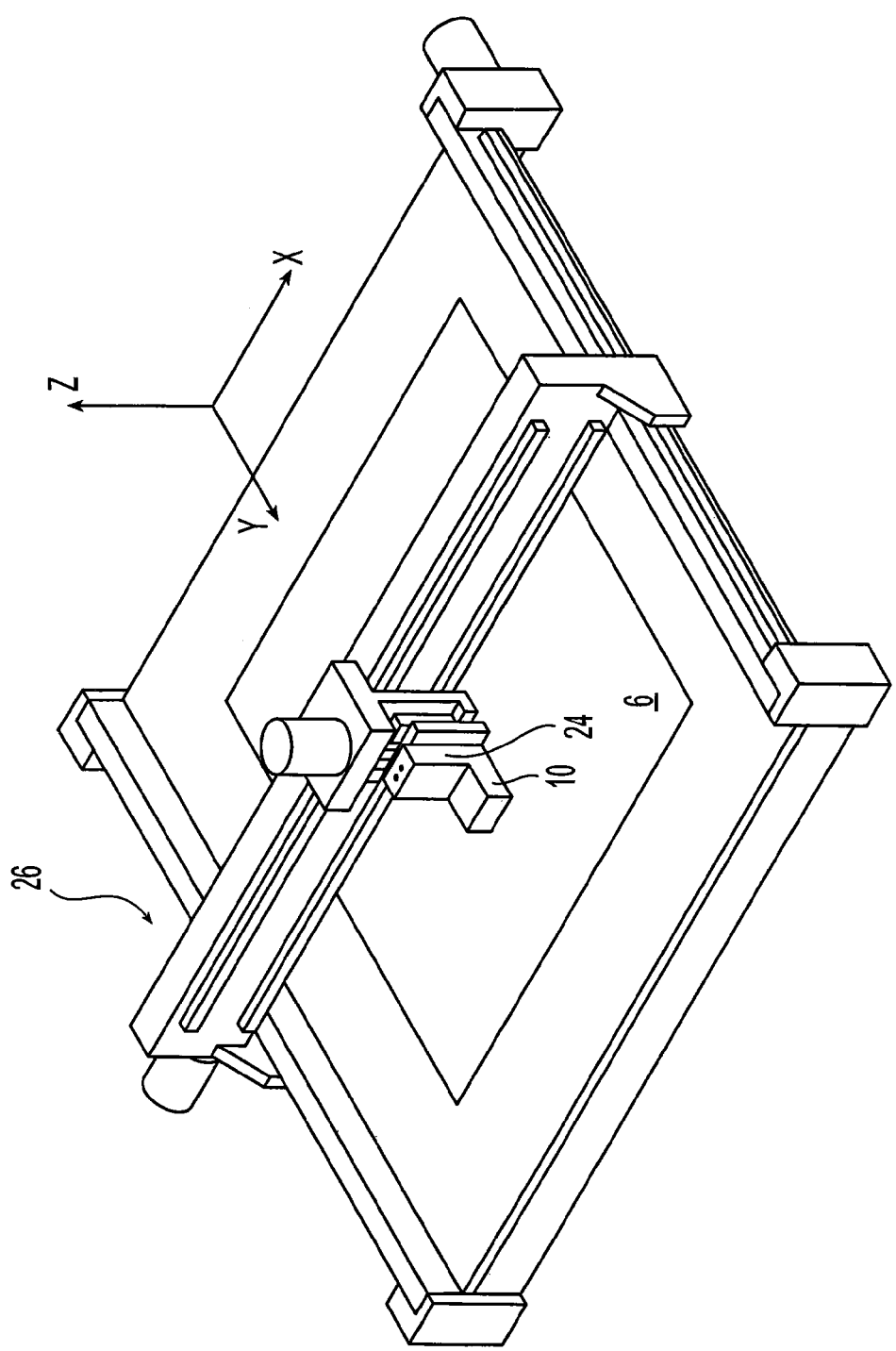
FIG. 7 is a perspective view of the single-coil test assembly, in the housing of FIG. 5, further installed in an automated positioning mechanism.

This single-coil tester assembly 10 is designed to be mounted via bracket 24 (see FIG. 7) to a positioning device 26, which may be used to precisely position the coil 4 at a desired location or locations adjacent the sample 6. The positioning device 26 will position the single-coil tester assembly 10 at a desired location with respect to the sample 6 in the x, y and z directions. Referring now to FIG. 7, the single-coil tester assembly 10 is shown installed in an exemplary positioning mechanism 26, which, in the illustrated embodiment is an adjustable gantry assembly such as an external CNC (Computer Numerically Controlled) x, y and z table assembly. The sample under test 6 is shown positioned beneath the single-coil tester assembly 10. The positioning of the single-coil tester assembly is provided by the CNC controller, thus allowing for precise and accurate x-axis, y-axis and z-axis positioning control. The x- and y-axis controls may be used to define where on the top surface of the sample 6 a particular measurement will be taken. A separate z-axis control may be provided to maintain the predetermined gap "G" between the single coil 4 and the sample 6. This positioning method ensures that accurate and repeatable measurement results may be obtained by providing a gap of known distance between single coil 4 and the sample 6. This arrangement also ensures maintenance of a desired magnetic flux density in proximity to the sample 6.

A variety of techniques may be used to adjust and verify the gap "G" between the coil 4 and sample 6 to ensure the accuracy of measured sheet resistance values. In one example, a pneumatic non-contact measurement system may be used to verify and control standoff distance (gap "G"), such as the SimgaTech Σ9600M, sold by SigmaTech, of Tempe Ariz. Alternatively, a fiberoptic non-contact measurement system may be used, such as a those sold by Philtec, Inc., of Annapolis, Md. Laser-based measurement systems are also contemplated.

These measurement systems may be used in combination with a feedback control system to verify the gap "G" and to automatically adjust the gap where necessary. Thus, the z-axis control may be verified at each test point, and the gap distance "G" adjusted prior to taking a reading. This verification can be either manually performed or it may be part of the overall system automation, to be controlled by computer 46 (see FIG. 10).

It will be appreciated that where the sample 6 comprises a wafer, flat panel, or the like, the sample may be handled (i.e., moved onto the positioning mechanism 26) using any of a variety of known automation techniques, such as robotic handlers and the like.

Although the inventive device has been described in relation to a single coil arrangement, it will be appreciated that a ringing coil (not shown) could be provided beneath the sample to be tested to provide a double coil arrangement. Such a double-coil arrangement may provide a wider range of allowable variance in the gap "G" between the coil 4 and the sample 6 under test while maintaining a desired accuracy (e.g., 3%) in system measurements.

Figure 8:
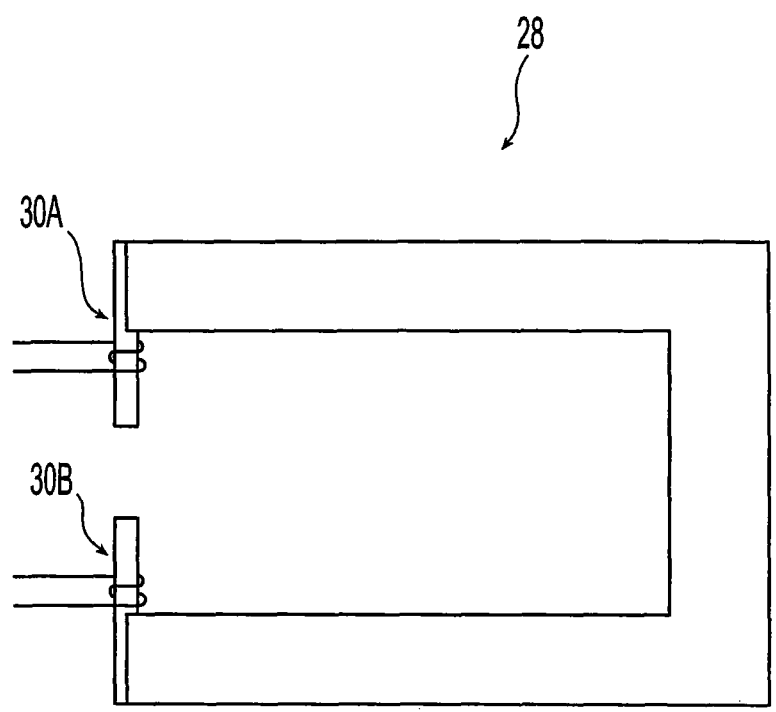
FIG. 8 is a plan view of an alternative coil arrangement.

An exemplary dual coil arrangement is shown in FIG. 8, in which a U-core coil 28 is provided having a ferrite material formed in the shape of the letter "U." Attached to each end of the "U" is a wire wound coil 30A, 30B. Both coils 30A, 30B will face each other, and may be rectangular or cylindrical rods of various sizes and/or shapes. The U-core coil 28 would utilize the same circuit board module 14 as described in relation to FIGS. 1 and 2, with the exception that the configuration shown in FIG. 8 would have a connection or "return" path between the cores of each coil 30A, 30B. The benefit of such a U-core coil is that it may result in a more uniform magnetic field in the space between the coils, since with traditional dual coil systems it is often difficult to provide both coils with identical inductance, since the coils may be hand wound. Thus, with a U-shaped core, a path is created between the coils 30A, 30B for the magnetic flux to be shared, and whatever inequality exists between the coils will be equalized.

Use of a dual core system such as described in relation to FIG. 8 may find applicability in scanning patient extremities, such as fingers or toes, or it may be used with very small patients.

As noted, the single coil test device may be particularly well suited for use in performing medical diagnostic procedures, such as verifying circulation and/or oxygenation of muscle tissue. Thus, the device may be used to scan patient limbs or appendages to obtain a non-invasive determination of the health of patient tissue due to changes of conductivity caused by either internal or external stimuli such as diseases, injury, or other medical causes affecting the health of biological tissues. The basic method used to measure biological tissue may be similar to that described previously regarding the measurement of sample 6. The tissue measurement technique may be manual or automated method.

It will be appreciated that although a "gantry"-type system has been described in which the coil 4 is moved into position relative to the test sample 6, it may also be possible to maintain the measurement coil(s) in fixed position and to move the sample into a desired proximity to the measurement coil(s). Alternatively, both the sample and the coil(s) could be movable with respect to each other. It will be further be appreciated that the size (area as well as thickness) of the sample to be measured using this system is only limited by the physical size of the positioning table and not the single coil tester assembly.

Figure 9:
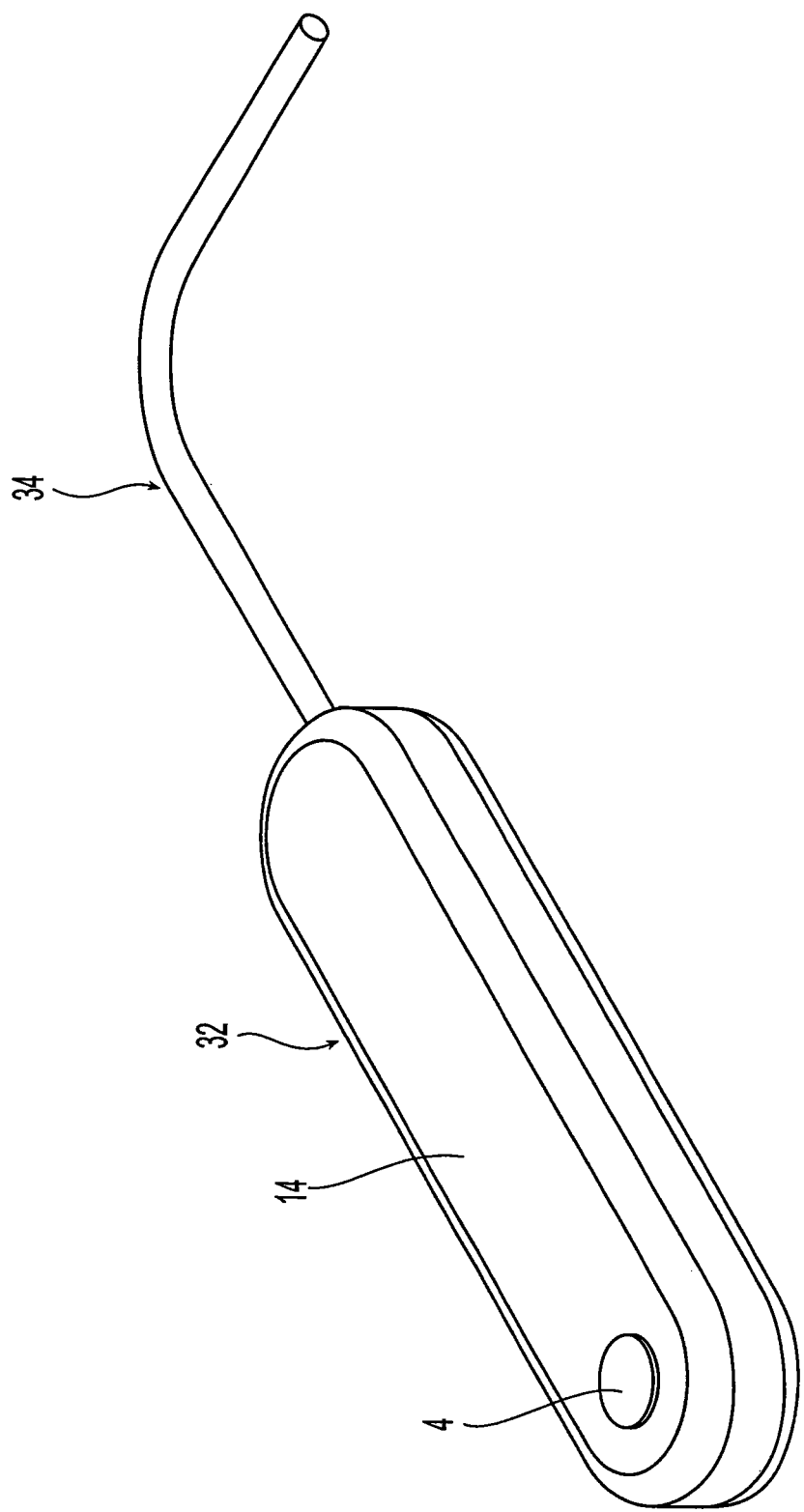
FIG. 9 is an isometric view of an alternative modular housing unit for the single coil test assembly.

Referring to FIG. 9, a handheld unit 32 is disclosed for use in a medical diagnostic application. The handheld unit 32 may enclose a single coil 4 and electronics module 14, and may be connected to an external power source and computer via cable 34. In use, the medical caregiver may position the coil sensor 4 on different areas of tissue to measure the conductance of the underlying tissue. For example, the unit 32 may be placed on the calf of a patient's leg to measure and record conductance using an associated computer or a microprocessor. The conductance information may be stored in memory, and comparisons may be drawn between the actual measured values of the patient tissue and stored "standard" conductance values associated with normal tissue conductance. Using such a comparison, a determination may be made regarding tissue health, which may assist the medical professional in making a diagnosis or treatment of tissue health.

Alternatively, the unit 32 may be strapped to an appendage for constant patient monitoring over a period of time in a variety of situations, such as during surgery or during a subsequent period of recovery. In one embodiment, the unit 32 may be battery powered and portable. Thus, the unit may be strapped to the patient and conductivity readings may be stored in onboard memory over a period of time. Periodically, the stored information may be downloaded for review by the doctor or other medical professional in order to facilitate a continuing diagnosis of patient condition. In one embodiment, the conductance information stored by the unit 32 may be downloaded to the patient's personal computer and sent to the medical professional via the Internet or other network.

Figure 10:
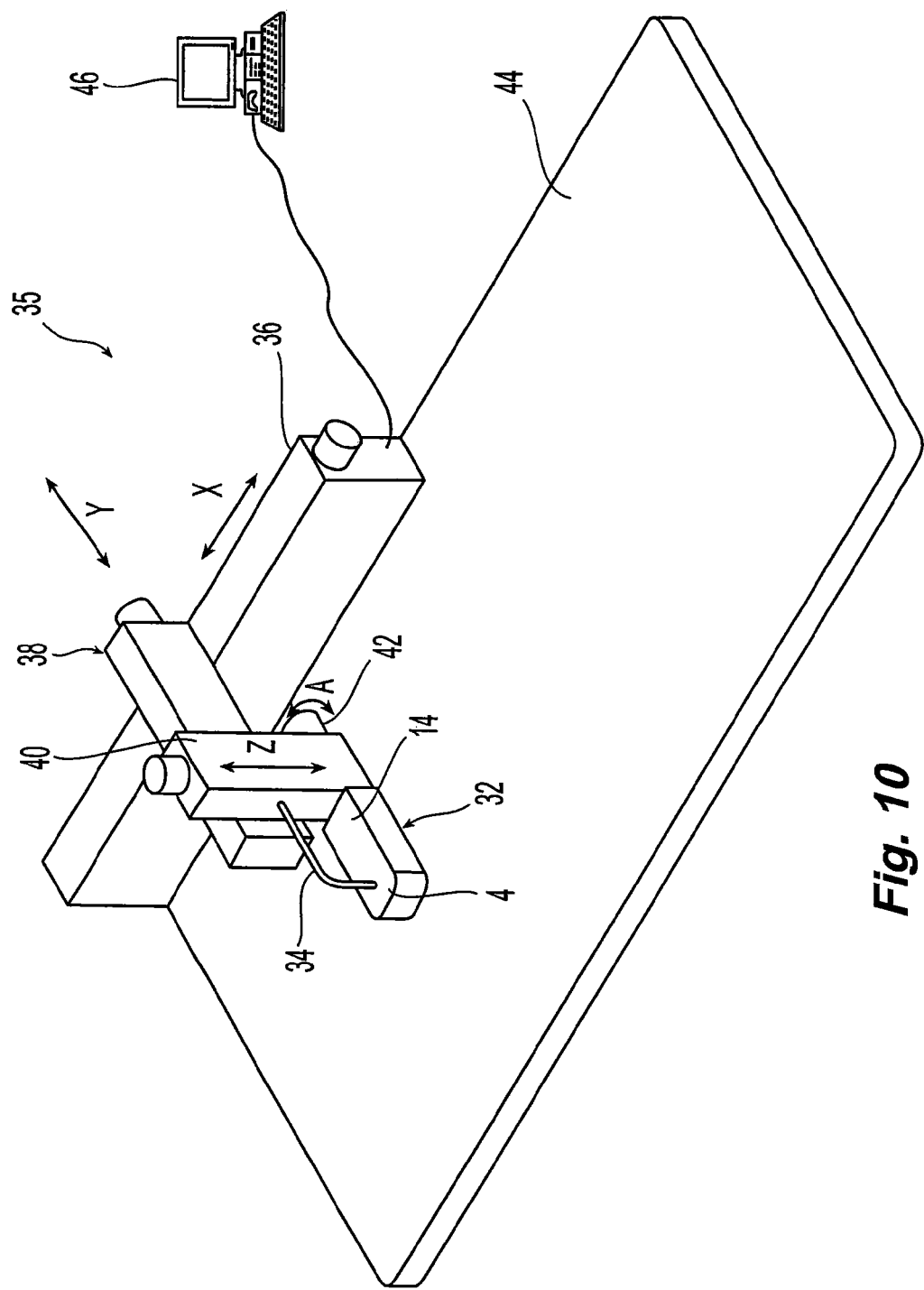
FIG. 10 is an isometric view of the modular housing unit of FIG. 9, installed in an automated positioning mechanism.

The handheld unit 32 may also be adapted for using with an automatic positioning system 35, such as that shown in FIG. 10. The automatic positioning system 35 may comprise x, y and z positioning elements 36, 38, 40 to enable automated movement of the coil 4 enclosed within unit 32. The positioning system 35 may further comprise may a rotational adjustment 42 to enable rotation of the coil 4 in the direction "A." The positioning system 35 may be mounted to a table 44 or platform upon which a patient may lay or be seated. In one embodiment, the positioning system 35 is controlled by a computer 46, which may move positioning elements 36, 38, 40 and rotational adjustment element 42 in response to specific operator inputs. The computer 46 may have a processor executing instructions to move the elements. The positioning elements and rotational adjustment element may move along a predetermined path under control of the computer. In one embodiment, the positioning system 35 may be used in combination with a pneumatic or fiberoptic offset measurement device as previously described to maintain a desired gap "G" over an uneven sample topography. A feedback loop may be provided to determine offset between the coil 4 and sample 6, and to automatically reposition one or more of the elements 36, 38, 40, 42 to maintain the desired gap "G" within a high level of precision.

The system may be adapted for use in scanning a patient while they are laying down (FIG. 10), or a positioning system 44 may be provided to accommodate other patient orientations. The system shown in FIG. 11 may be used, for example, to scan a standing patient's leg. The patient may stand on a platform 47, with the coil 4 and electronics module 14 positioned for vertical and horizontal movement with respect to the platform. A pair of motors 48, 40 may be provided to move the coil 4 along the contours of the leg, aided by a computerized control and feedback loop as previously described in relation to the system of FIG. 10, to maintain a predetermined gap distance between the coil sensor and the surface being measured.

Figure 11:
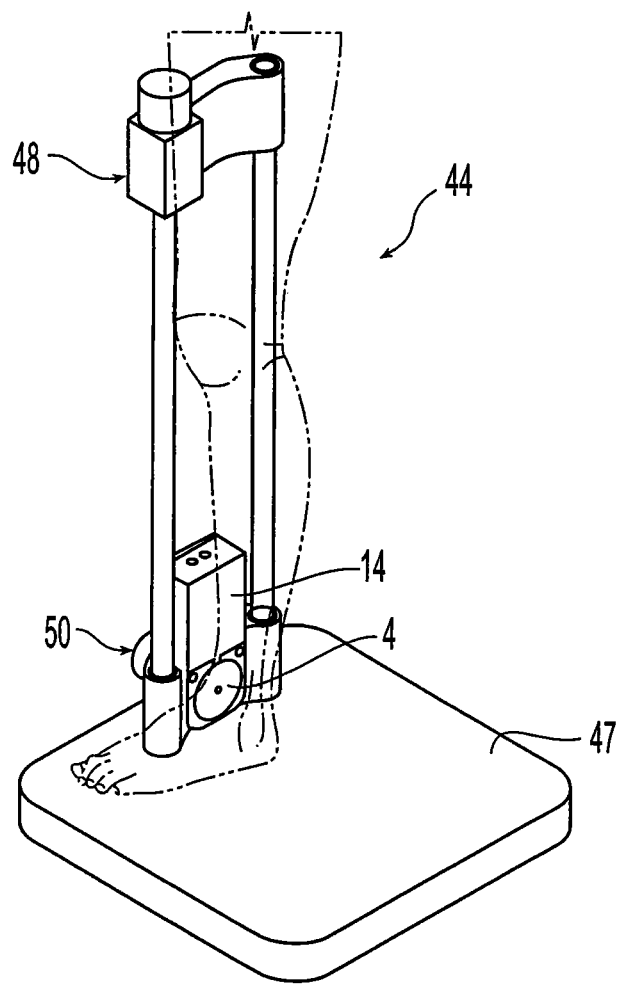
FIG. 11 is an isometric view of a further alternative automated positioning mechanism.

Additional controls or options to the automatic positioning systems of FIGS. 10 and 11 may add the ability to scan different sides of a patient measurement area, resulting in the construction of a 3D map of tissue conductance. Additionally, appropriate controls may be provided to allow the adjustment/positioning system to "learn" a particular path for scanning a specific patient's anatomy. Thus, in one example, the coil 4 may be manually positioned and moved along a desired path, such as the path of an artery down a patient's leg. The movements of the coil 4 could be stored in memory and used during subsequent scans to move along the same path, thus minimizing the time required to perform follow up scans.

This repeatability may be useful for performing daily or weekly tracking measurements of circulation for patients taking blood thinner drugs to treat conditions such as tissue ischemia, to determine whether the patient is improving, stabilizing or worsening. Additionally, the described technique could be used in a research capacity by drug companies to determine how well drugs are absorbed into the blood stream.

Additionally, the system may be adapted to diagnosing internal injuries, such as internal bleeding, where little or no external indication of injury is available. For example, a coil 4 may be used to measure blood conductance, in particular to detect the pooling of blood in the body. Abnormally high conductance may be indicative of such pooling, and thus a trauma patient may be monitored over time to determine whether such bleeding is present. One clear example of the utility of such a detection method would be in the prioritization of treatment of patients (i.e., in triage) during wartime where a large number of patients are processed and where quick and easy monitoring of blood conductance could result in the identification of a severely injured soldier who may otherwise have few externally visible injuries.

Further, the automated positioning systems and conductance measurement electronics may be adaptable for measuring structures such as metallic or non-metallic aircraft wings, fuselage, or other structures in which the ongoing integrity of the structure is of critical importance.

It will be understood that the description and drawings presented herein represent an embodiment of the invention, and are therefore merely representative of the subject matter that is broadly contemplated by the invention. It will be further understood that the scope of the present invention encompasses other embodiments that may become obvious to those skilled in the art, and that the scope of the invention is accordingly limited by nothing other than the appended claims.

The invention claimed is:

1. A method for measuring conductance of a sample, comprising:
    providing a coil, an oscillator connected to the coil for applying a voltage to the coil to induce a magnetic field, and an automatic gain control circuit connected to the oscillator;
    positioning said coil adjacent a sample to be measured;
    subjecting the sample to a magnetic field produced by said coil;
    detecting a change in voltage due to the presence of said sample in said magnetic field;
    converting said voltage change to a conductance value for said sample; and
    comparing said conductance value to a standard conductance value to determine whether said conductance value is within a predetermined acceptable range,
    wherein the sample has a contoured surface, the method further comprising the step of moving the coil along the contoured surface of the sample while maintaining a predetermined gap distance between the coil and the contoured surface being measured.

2. The method of claim 1, wherein the step of positioning said coil comprises moving said coil to a predetermined offset distance from the sample.

3. The method of claim 1, wherein the step of positioning said coil comprises adjusting the position of said coil using an automatic positioning system subject to computer control.

4. The method of claim 1, wherein said sample is a portion of a human patient, the method further comprising the step of storing said conductance value and said standard conductance value in a memory element associated with said coil; and wherein said step of comparing said conductance value to a standard conductance value further comprises developing trend information regarding conductance values for said sample and using said trend information to make a treatment decision regarding a patient.

5. The method of claim 1, wherein the step of comparing said conductance value to a standard conductance value further comprises comparing a plurality of individual conductance values of the sample measured at a plurality of measurement locations, and comparing said individual conductance values to a plurality of respective standard conductance values.

6. The method of claim 3, wherein adjusting the position of the coil includes automatically adjusting the position of said coil with respect to said sample to maintain a predetermined distance between said coil and said sample.

7. The method of claim 1, wherein the coil is a single ferrite cup coil.

8. The method of claim 1, further comprising the steps of:
    measuring a voltage when the coil is inducing a magnetic field in the absence of the coil being positioned adjacent the sample such that the sample is not in the presence of the magnetic field,
    wherein the change in voltage is relative to the voltage measured when the coil is inducing the magnetic field in the absence of the coil being positioned adjacent the sample.

9. The method of claim 1, wherein in order to correlate the voltage change to a conductance value of the sample, a calibration is provided, using a standard wafer, tissue phantom or similar calibration sample having known properties.

10. The method of claim 1, further comprising the step of positioning the sample on a platform, wherein the coil is configured for vertical and horizontal movement with respect to the platform.

11. The method of claim 1, further comprising the step of positioning the single coil to perform measurements on at least two different sides of said contoured sample.

12. The method of claim 1, further comprising providing a plurality of individual conductance values of the sample measured at a plurality of measurement locations, and comparing said individual conductance values to a plurality of respective standard conductance values, wherein the determining step determines whether said conductance values of the sample are within the predetermined acceptable range.

* * * * *